(12) United States Patent
Smart et al.

(10) Patent No.: US 11,111,463 B2
(45) Date of Patent: Sep. 7, 2021

(54) SOLID CLEANSING COMPOSITIONS WITH TAURINE AND METHODS THEREOF

(71) Applicant: Colgate-Palmolive Company, New York, NY (US)

(72) Inventors: Scott Smart, Piscataway, NJ (US); Long Pan, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 301 days.

(21) Appl. No.: 16/323,821

(22) PCT Filed: Aug. 8, 2016

(86) PCT No.: PCT/US2016/046012
§ 371 (c)(1),
(2) Date: Feb. 7, 2019

(87) PCT Pub. No.: WO2018/030983
PCT Pub. Date: Feb. 15, 2018

(65) Prior Publication Data
US 2019/0169548 A1    Jun. 6, 2019

(51) Int. Cl.
| | | |
|---|---|---|
| C11D 1/00 | (2006.01) |
| C11D 9/02 | (2006.01) |
| C11D 9/30 | (2006.01) |
| C11D 9/32 | (2006.01) |
| A61K 8/02 | (2006.01) |
| A61K 8/42 | (2006.01) |
| A61Q 19/10 | (2006.01) |
| A61K 8/46 | (2006.01) |
| C11D 11/00 | (2006.01) |
| C11D 17/00 | (2006.01) |

(52) U.S. Cl.
CPC ............. *C11D 9/02* (2013.01); *A61K 8/0216* (2013.01); *A61K 8/42* (2013.01); *A61K 8/466* (2013.01); *A61Q 19/10* (2013.01); *C11D 9/30* (2013.01); *C11D 9/32* (2013.01); *C11D 11/0082* (2013.01); *C11D 17/0047* (2013.01); *A61K 2800/52* (2013.01)

(58) Field of Classification Search
CPC ................................ C11D 9/02; A61K 8/0216
See application file for complete search history.

(56) References Cited

U.S. PATENT DOCUMENTS

| | | |
|---|---|---|
| 8,557,228 B2 | 10/2013 | Pan et al. |
| 8,663,610 B2 | 3/2014 | Pappas et al. |
| 8,815,222 B2 | 8/2014 | Pan et al. |
| 9,856,441 B2 | 1/2018 | Gu et al. |
| 2014/0178315 A1* | 6/2014 | Gruber ............... A61K 8/416 424/59 |
| 2017/0335251 A1* | 11/2017 | Nabi .................. C11D 3/349 |
| 2019/0008739 A1* | 1/2019 | Nabi .................. A61Q 19/00 |

FOREIGN PATENT DOCUMENTS

RU    2272613    3/2006

OTHER PUBLICATIONS

International Search Report and Written Opinion of the International Searching Authority in International Application No. PCT/US2016/046012, dated May 2, 2017.

* cited by examiner

*Primary Examiner* — Necholus Ogden, Jr.

(57) ABSTRACT

A solid liquid cleansing composition and methods of preparing the same are disclosed. The solid cleansing composition may include a soap and an ionic liquid. The soap may be a sodium soap, an ammonium soap, a potassium soap, a magnesium soap, a calcium soap, or a combination thereof. The ionic liquid may include a base, taurine, and/or water.

20 Claims, No Drawings

SOLID CLEANSING COMPOSITIONS WITH TAURINE AND METHODS THEREOF

BACKGROUND

Conventional cosmetic and personal care compositions (e.g., hair conditioners, moisturizers, cleansing products, shaving cream, after-shaves, etc.) may often include one or more ingredients (e.g., perfumes, preservatives, surfactants, etc.) that may strip moisture from the skin, thereby leaving the skin feeling overly dry or chapped. Accordingly, conventional cosmetic and personal care compositions often include taurine and derivatives thereof to maintain hydration of the skin. In addition to maintaining hydration of the skin, the incorporation of taurine may also contribute to maintenance of the skin barrier, reduction of inflammation, and/or reduction of skin irritation.

While taurine has shown efficacy in promoting healthy skin, it is typically only incorporated in non-solid cosmetic and personal care compositions (e.g., gels, creams, lotions, liquids, etc.), as incorporating taurine in solid cosmetic and personal care compositions (e.g., bar soaps) in effective or appreciable quantities has proved to be substantially more difficult. For example, incorporating taurine in bar soaps in effective or appreciable quantities often leads to the precipitation or crystallization of taurine on surfaces thereof, which leads to an unwelcome abrasive feeling.

What is needed, then, are improved solid cleansing or cosmetic and personal care compositions incorporating taurine and methods for solubilizing taurine.

BRIEF SUMMARY

This summary is intended merely to introduce a simplified summary of some aspects of one or more embodiments of the present disclosure. Further areas of applicability of the present invention will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing a solid cleansing composition including a soap and an ionic liquid. The ionic liquid of the solid cleansing composition may include a base and taurine.

In another embodiment, the ionic liquid may be an anhydrous ionic liquid having less than 0.5 wt % water based on a total weight of the ionic liquid.

In another embodiment, the ionic liquid may comprises water.

In another embodiment, the ionic liquid may be a hydrated ionic liquid having greater than or equal to 0.5 wt % water based on a total weight of the ionic liquid.

In another embodiment, a molar ratio of the base to taurine may be greater than or equal to 1:1.

In another embodiment, a molar ratio of the base to taurine may be greater than 1:1 and less than or equal to 3:1.

In another embodiment, a molar ratio of the base to taurine may be greater than 1:1 and less than or equal to 2.5:1.

In another embodiment, a molar ratio of the base to taurine may be greater than 1:1 and less than or equal to 2:1.

In another embodiment, a molar ratio of taurine to water may be greater than or equal to 1:1.

In another embodiment, a molar ratio of taurine to water may be greater than 1:1 and less than or equal to 3:1.

In another embodiment, a molar ratio of taurine to water may be greater than 1:1 and less than or equal to 2:1.

In another embodiment, the base may be urea.

In another embodiment, the soap may be a sodium soap, an ammonium soap, a potassium soap, a magnesium soap, a calcium soap, or a combination thereof.

In another embodiment, the soap may be or include alkali metal salts of aliphatic acids having 8 to 22 carbon atoms.

The foregoing and/or other aspects and utilities embodied in the present disclosure may also be achieved by providing a method for preparing the solid cleansing composition. The method may include contacting the base with taurine, and heating the base and taurine to form the ionic liquid. The method may also include contacting the ionic liquid with the soap.

In another embodiment, the method may include contacting the base with water to form a slurry before contacting the base with taurine.

In another embodiment, the method may include contacting the taurine with the slurry before heating the base and taurine.

In another embodiment, the method may include heating the base and taurine comprises heating the base and taurine to a temperature greater than 80° C.

In another embodiment, the method may include melting the base before solubilizing taurine.

The foregoing and/or other aspects and utilities embodied in the present disclosure may also be achieved by providing a solid cleansing composition including a soap an ionic liquid. The soap may be selected from a sodium soap, an ammonium soap, a potassium soap, a magnesium soap, a calcium soap, or a combination thereof. The ionic liquid may include urea and taurine. The ionic liquid may be an anhydrous ionic liquid having less than 0.05 wt % water based on a total weight of the ionic liquid. A molar ration of the urea to taurine in the ionic liquid may be greater than 1:1 and less than or equal to 3:1.

Further areas of applicability of the present invention will become apparent from the detailed description provided hereinafter. It should be understood that the detailed description and specific examples, while indicating some preferred aspects of the invention, are intended for purposes of illustration only and are not intended to limit the scope of the invention.

DETAILED DESCRIPTION

The following description of various preferred aspect(s) is merely exemplary in nature and is in no way intended to limit the invention, its application, or uses.

As used throughout, ranges are used as shorthand for describing each and every value that is within the range. Any value within the range may be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material. Ratios disclosed herein should be understood to refer to molar ratios. For example, a 1:1 taurine:urea mixture is 1 mol of taurine to 1 mol of urea.

Additionally, all numerical values are "about" or "approximately" the indicated value, and take into account experimental error and variations that would be expected by a person having ordinary skill in the art. It should be appreciated that all numerical values and ranges disclosed herein are approximate valves and ranges, whether "about" is used in conjunction therewith. It should also be appreciated that the term "about," as used herein, in conjunction with a numeral refers to a value that may be +/−1% (inclusive) of that numeral, +/−2% (inclusive) of that numeral, +/−3% (inclusive) of that numeral, +/−5% (inclusive) of that numeral, +/−10% (inclusive) of that numeral, or +/−15% (inclusive) of that numeral. It should further be appreciated that when a numerical range is disclosed herein, any numerical value falling within the range is also specifically disclosed.

Compositions

It has been surprisingly and unexpectedly discovered that taurine may be incorporated into solid cleansing compositions, such as bar soap compositions, via a eutectic system or an ionic liquid thereof. Particularly, combining taurine with a base, such as urea, may form a eutectic system or provide an ionic liquid that may be incorporated into the solid cleansing compositions (e.g., the bar soap compositions). Without being bound by theory, it is believed that incorporating the urea into the eutectic system or the ionic liquid prevents taurine from precipitating or crystallizing when contacted, mixed, or otherwise combined with a cleansing component (e.g., a soap) of the solid cleansing compositions. It has further been surprisingly and unexpectedly discovered that the ionic liquid maintains or preserves color of the solid cleansing compositions, and contributes to the overall moisture of the solid cleansing compositions.

Eutectic System

The eutectic system or the ionic liquid thereof may include taurine, a base, and optionally water. For example, the ionic liquid may be a hydrated ionic liquid including taurine, the base, and water. In another example, the ionic liquid may be an anhydrous ionic liquid including only taurine and the base. As used herein, the term "anhydrous ionic liquid" or "anhydrous eutectic system" may refer to an ionic liquid or eutectic system that contains water in an amount less than 0.5 wt %, less than 0.4 wt %, less than 0.3 wt %, less than 0.2 wt %, less than 0.1 wt %, less than 0.05 wt %, less than 0.04 wt %, less than 0.03 wt %, less than 0.02 wt %, less than 0.01 wt %, less than 0.005 wt %, or less than 0.0001 wt %, based on a total weight of the ionic liquid. Further, as used herein, the term "hydrated ionic liquid" or "hydrous eutectic system" may refer to an ionic liquid or eutectic system that contains water in an amount greater than or equal to 0.5 wt %, based on a total weight of the ionic liquid. It should be appreciated that water for the purpose of preparing the active of the eutectic system and the ionic liquid thereof is separate from water in other portions of the solid cleansing composition (e.g., cleansing component, fragrances, etc.). The water, however, may be considered in the final active.

In at least one embodiment, the hydrated ionic liquid includes water in an amount greater than or equal to 0.5 wt % and less than or equal to 4 wt %. For example, the amount of water in the hydrated ionic liquid may be about 0.5 wt %, about 1.0 wt %, about 1.5 wt %, or about 2.0 wt % to about 2.5 wt %, about 3.0 wt %, about 3.5 wt %, or about 4.0 wt %. In another embodiment, the amount of water in the hydrated ionic liquid may be greater than or equal to 4.0 wt % and less than or equal to 20 wt %, based on a total weight of the ionic liquid. For example, the amount of water in the hydrated ionic liquid may be about 4.0 wt %, about 5.0 wt %, about 6.0 wt %, about 7.0 wt %, about 8.0 wt %, about 9.0 wt %, about 10.0 wt %, or about 11.0 wt % to about 12.0 wt %, about 13.0 wt %, about 14.0 wt %, about 15.0 wt %, about 16.0 wt %, about 17.0 wt %, about 18.0 wt %, about 19.0 wt %, or about 20.0 wt %. In yet another embodiment, the amount of water in the hydrated ionic liquid may be greater than or equal to 15.0 wt % and less than or equal to 50 wt %, based on a total weight of the ionic liquid. For example, the amount of water in the hydrated ionic liquid may be about 15 wt %, about 20 wt %, about 25 wt %, or about 30 wt % to about 35 wt %, about 40 wt %, about 45 wt %, or about 50 wt %.

In at least one embodiment, a molar ratio of taurine or the base (e.g., urea) to water may be greater than or equal to about 1:1 and less than or equal to about 3:1. For example, the molar ratio of taurine or the base (e.g., urea) to water may be about 1:1, about 1.1:1, about 1.2:1, about 1.3:1, about 1.4:1, about 1.5:1, about 1.6:1, about 1.7:1, about 1.8:1, about 1.9:1, about 2:1, about 2.1:1, about 2.2:1, about 2.3:1, about 2.4:1, about 2.5:1, about 2.6:1, about 2.7:1, about 2.8:1, about 2.9:1, or about 3:1. In another example, the molar ratio of taurine or the base (e.g., urea) to water may be from about 1:1, about 1.1:1, about 1.2:1, about 1.3:1, about 1.4:1, about 1.5:1, about 1.6:1, about 1.7:1, about 1.8:1, or about 1.9:1 to about 2:1, about 2.1:1, about 2.2:1, about 2.3:1, about 2.4:1, about 2.5:1, about 2.6:1, about 2.7:1, about 2.8:1, about 2.9:1, about 3:1, or greater. In another example, the molar ratio of the base (e.g., urea) to water may be greater than 1:1, greater than 1.1:1, greater than 1.2:1, greater than 1.3:1, greater than 1.4:1, greater than 1.5:1, greater than 1.6:1, greater than 1.7:1, greater than 1.8:1, or greater than 1.9:1. In another example, the molar ratio of taurine or the base (e.g., urea) to water may be about 1:1 to about 3:1, about 1.1:1 to about 2.9:1, about 1.2:1 to about 2.8:1, about 1.3:1 to about 2.7:1, about 1.4:1 to about 2.6:1, about 1.5:1 to about 2.5:1, about 1.6:1 to about 2.4:1, about 1.7:1 to about 2.3:1, about 1.8:1 to about 2.2:1, or about 1.9:1 to about 2.1:1. In a preferred embodiment, the molar ratio of taurine or the base (e.g., urea) to water is about 2:1.

The base of the eutectic system may be or include one or more hydrogen bond donors or Brønsted bases. The hydrogen bond donor or the Brønsted base of the eutectic system may be or include, but is not limited to, urea, arginine, lysine, acetamide, guanidine, and the like, and combinations thereof. In a preferred embodiment, the base of the eutectic system is urea.

The amount or concentration of the base in the eutectic system may vary widely. In at least one embodiment, the amount of the base in the eutectic system may depend, at least in part, on the amount of taurine in the eutectic system. For example, the amount of the base provided in the eutectic system may be an amount sufficient to form the ionic liquid with all of the taurine in the eutectic system. The amount of the base provided in the eutectic system may alternatively be greater than an amount sufficient to form the ionic liquid with all of the taurine in the eutectic system.

In at least one embodiment, a molar ratio of the base (e.g., urea) to taurine may be greater than or equal to about 1:1 and less than or equal to about 3:1. For example, the molar ratio of the base (e.g., urea) to taurine may be about 1:1, about 1.1:1, about 1.2:1, about 1.3:1, about 1.4:1, about 1.5:1, about 1.6:1, about 1.7:1, about 1.8:1, about 1.9:1, about 2:1, about 2.1:1, about 2.2:1, about 2.3:1, about 2.4:1, about 2.5:1, about 2.6:1, about 2.7:1, about 2.8:1, about 2.9:1, or about 3:1. In another example, the molar ratio of the base (e.g., urea) to taurine may be from about 1:1, about 1.1:1, about 1.2:1, about 1.3:1, about 1.4:1, about 1.5:1, about 1.6:1, about 1.7:1, about 1.8:1, or about 1.9:1 to about 2:1, about 2.1:1, about 2.2:1, about 2.3:1, about 2.4:1, about 2.5:1, about 2.6:1, about 2.7:1, about 2.8:1, about 2.9:1, about 3:1, or greater. In another example, the molar ratio of the base (e.g., urea) to taurine may be greater than 1:1, greater than 1.1:1, greater than 1.2:1, greater than 1.3:1, greater than 1.4:1, greater than 1.5:1, greater than 1.6:1, greater than 1.7:1, greater than 1.8:1, or greater than 1.9:1. In another example, the molar ratio of the base (e.g., urea) to taurine may be about 1:1 to about 3:1, about 1.1:1 to about 2.9:1, about 1.2:1 to about 2.8:1, about 1.3:1 to about 2.7:1, about 1.4:1 to about 2.6:1, about 1.5:1 to about 2.5:1, about 1.6:1 to about 2.4:1, about 1.7:1 to about 2.3:1, about 1.8:1 to about 2.2:1, or about 1.9:1 to about 2.1:1. In a preferred embodiment, the molar ratio of the base (e.g., urea) to taurine is about 2:1.

In at least one embodiment, taurine of the eutectic system may be provided as a free form (i.e., 2-aminoethanesulfonic acid). In another embodiment, taurine of the eutectic system may be provided in a salt form. For example, taurine may be in a base addition salt form, such as an alkali metal salt, an alkaline earth metal salt, an ammonium salt, and the like, and combinations thereof. Illustrative salt forms of taurine may include, but are not limited to, sodium salts, potassium salts, lithium salts, calcium salts, magnesium salts, ammonium salts, tetralkylammonium salts, and the like, and combinations thereof.

The base, taurine, and optionally water may be contacted, mixed, blended, or otherwise combined with one another to produce the ionic liquid of the eutectic system. In at least one embodiment, the base may be contacted or combined with taurine, and water may optionally be combined with the base and taurine. For example, the base and taurine may be combined with one another to form the anhydrous ionic liquid, and the water may be subsequently combined with the anhydrous ionic liquid to produce the hydrated ionic liquid. In another embodiment, the base, taurine, and optionally water may be combined with one another in a single step to form the ionic liquid. In a preferred embodiment, the base may be combined with water to form a slurry, and the taurine may be combined with the slurry to produce the hydrated ionic liquid. In at least one embodiment, the base, taurine, and optionally water may be combined with one another under heat. For example, the base, taurine, and optionally water may be heated (e.g., reflux, oven/furnace, etc.) to form the ionic liquid (i.e., the anhydrous and/or the hydrated ionic liquid). In at least one embodiment, the base and taurine may be heated to a temperature greater than or equal to 115° C. and less than or equal to 160° C. to form the anhydrous ionic liquid. In another embodiment, the base, taurine, and water may be heated to a temperature greater than 60° C. and less than 120° C. to form the hydrated ionic liquid.

The anhydrous or hydrated ionic liquid may have a melting point greater than or equal to 0° C. and less than or equal to 100° C. For example, the ionic liquid may be a liquid between 0° C. and 100° C. In another example, the ionic liquid may be a liquid at room temperature, or about 21° C. In at least one embodiment, the melting point of the ionic liquid may be less than taurine and the base. For example, in a preferred embodiment, the melting point of the ionic liquid is less than both taurine (melting point=305.1° C.) and urea (melting point=133° C.).

The amount or concentration of the ionic liquid in the solid cleansing composition may vary widely. In at least one embodiment, the amount of the ionic liquid in the solid cleansing composition may be greater than 0 wt % and less than or equal to about 10 wt %. For example, the amount of the ionic liquid in the solid cleansing composition may be about 0.01 wt %, about 1 wt %, about 2 wt %, about 3 wt %, about 4 wt %, or about 5 wt % to about 6 wt %, about 7 wt %, about 8 wt %, about 9 wt %, or about 10 wt %. In another example, the amount of the ionic liquid in the solid cleansing composition may be about 0.01 wt % to about 10 wt %, about 1 wt % to about 9 wt %, about 2 wt % to about 8 wt %, about 3 wt % to about 7 wt %, or about 4 wt % to about 6 wt %. In at least one embodiment, the amount of the ionic liquid in the solid cleansing composition may be greater than 10 wt % and less than or equal to about 80 wt %. For example, the amount of the ionic liquid in the solid cleansing composition may be about 10 wt %, about 15 wt %, about 20 wt %, about 25 wt %, about 30 wt %, about 35 wt %, about 40 wt %, or about 45 wt % to about 50 wt %, about 55 wt %, about 60 wt %, about 65 wt %, about 70 wt %, about 75 wt %, or about 80 wt %. In another example, the amount of the ionic liquid in the solid cleansing composition may be about 10 wt % to about 80 wt %, about 15 wt % to about 75 wt %, about 20 wt % to about 70 wt %, about 25 wt % to about 65 wt %, about 30 wt % to about 60 wt %, about 35 wt % to about 55 wt %, or about 40 wt % to about 50 wt %.

Cleansing Component

The solid cleansing composition may include at least one cleansing component. In at least one embodiment, the cleansing component may include a base component, such as a soap or a soap chip. The base component or the soap may be or include alkali metal or alkanol ammonium salts of aliphatic alkane- or alkene-monocarboxylic acids. Sodium, magnesium, potassium, calcium, mono-, di-, tri-ethanol ammonium cations, and the like, and combinations thereof, may be suitable for the solid cleansing composition disclosed herein. In a preferred embodiment, the soap of the cleansing component includes a sodium soap. While a sodium soap is preferred, it should be appreciated that at least a portion of the soap may include one or more ammonium soaps, potassium soaps, magnesium soaps, calcium soaps, and the like, and combinations thereof. The base component or the soap may be or include, but is not limited to, alkali metal salts of aliphatic (alkanoic or alkenoic) acids having about 8 to about 22 carbon atoms, and preferably about 10 to about 20 carbon atoms.

The amount or concentration of the soap in the cleansing component may vary widely. In at least one embodiment, the amount of the soap (e.g., the sodium soap) in the cleansing component may be greater than or equal to 50 wt % and less than or equal to 95 wt %. For example, the amount of the soap in the cleansing component may be from about 50 wt %, about 55 wt %, about 60 wt %, about 65 wt %, or about 70 wt % to about 75 wt %, about 80 wt %, about 85 wt %, about 90 wt %, or about 95 wt %. In a preferred embodiment, the amount of the soap in the cleansing component is greater than 70 wt % and less than 80 wt %. For example, the amount of the soap in the cleansing component may be from about 70 wt %, about 71 wt %, about 72 wt %, about 73 wt %, about 74 wt %, or about 75 wt % to about 76 wt %, about 77 wt %, about 78 wt %, about 79 wt %, or about 80 wt %. As discussed above, in a preferred embodiment, the cleansing component includes a sodium soap. It should be appreciated, however, that the soap of the cleansing composition may include about 1% to about 25% of any one or more of the ammonium soaps, the potassium soaps, the magnesium soaps, the calcium soaps, and the like, and combinations thereof.

The soap of the cleansing component may be or include one or more surfactants. For example, the soap may include one or more anionic surfactants, one or more amphoteric surfactants, one or more cationic surfactants, one or more zwitterionic surfactants, one or more nonionic surfactants, and mixtures thereof. Examples of suitable surfactants may be found in U.S. Pat. No. 3,959,458 to Agricola et al., U.S. Pat. No. 3,937,807 to Haefele, and U.S. Pat. No. 4,051,234 to Gieske et al., the disclosures of which are incorporated herein by reference. Any other surfactant may also be present in the soap including, but not limited to, sulfate, sulfonate alpha olefin sulfonates, isethionates such as SCI, N-alkyl or N-acyl taurates, sulfosuccinate, phosphates, glycinates, amphoteric surfactants such as betaines, sulfobetaines and the like and nonionic surfactants such as alkanolamide, alkylpolyglycosides.

Water

The solid cleansing composition and the cleansing component thereof may include water. Water of the solid cleansing composition and the cleansing component thereof may be deionized water, demineralized water, and/or softened water. Water of the cleansing component may be separate from the water of the ionic liquid. For example, water of the soap may be separate from water in the hydrated ionic liquid. Water may make up the balance of the solid cleansing composition. For example, the amount of water in the solid cleansing composition may be from about 10 wt % to 20 wt %, about 12 wt % to about 18 wt %, or about 14 wt % to about 16 wt %. In another example, the amount of water in the solid cleansing composition may be at least 10 wt %, at least 11 wt %, at least 12 wt %, at least 13 wt %, at least 14 wt %, at least 15 wt %, at least 16 wt %, or at least 17 wt %. In at least one embodiment, the amount of water may be about 10 wt %, about 11 wt %, about 12 wt %, about 13 wt %, about 14 wt %, or about 15 wt % The amount of water in the solid cleansing composition may include free water added and water introduced with other components or materials of the solid cleansing composition. For example, the amount of water in the solid cleansing composition may include free water and water associated with the soap (i.e., the cleansing component), the eutectic system, and/or the ionic liquid thereof, or any other component of the solid cleansing composition.

Humectants

The solid cleansing composition may include one or more humectants. Illustrative humectants may include, but are not limited to, ascorbic acid, ascorbyl dipalmitate, acetamide MEA, glucose glutamate, glucuronic acid, TEA-lactate, TEA-PCA, corn syrup, fructose, glucose, glycerin, glycol, 1,2,6-hexanetriol, sodium lactate, sodium PCA, hydrogenated starch hydrolysate, inositol, lactic acid, lactose, mannitol, PCA, PEG-10 propylene glycol, polyamino sugar condensate, propylene glycol, pyridoxine dilaurate, saccharide hydrolysate, hydroxystearyl methylglucamine, glucamine, maltitol, mannitol, methyl gluceth-10, methyl gluceth-20, riboflavin, PEG-4, PEG-6, PEG-8, PEG-9, PEG-10, PEG-12, PEG-14, PEG-16, PEG-18, PEG-20, PEG-32, PEG-40, glutamic acid, glycereth-7, glycereth-12, glycereth-26, saccharide isomerate, sorbeth-20, sorbitol, sucrose, thioglycerin, tris-(hydroxymethyl)nitromethane, tromethamine, histidine, PEG-75, PEG-135, PEG-150, PEG-200, PEG-5 pentaerythritol ether, polyglyceryl sorbitol, sorbitol, urea, xylitol, and the like, and combinations thereof.

In at least one embodiment, the humectant may be at least partially provided by the eutectic system. For example, the eutectic system may include taurine and urea, and urea may be configured to form an ionic liquid with taurine and provide humectant properties to the solid cleansing composition. In another example, urea of the eutectic system may be provided in an amount such that urea associated with the eutectic system does not contribute humectant properties to the solid cleansing composition. It should be appreciated that the ability of urea to provide or contribute humectant properties to the solid cleansing composition may be at least partially determined by the amount of urea in the solid cleansing composition and/or the eutectic system thereof. The ability of urea to provide humectant properties to the solid cleansing composition may also be at least partially determined by the ratio of urea to taurine in the eutectic system. In yet another embodiment, the ability of urea to provide humectant properties to the solid cleansing composition may also be at least partially determined by the method of producing the solid cleansing composition. For example, the urea and the taurine may be contacted, mixed, or otherwise combined with one another to form the ionic liquid prior to combining the ionic liquid with the cleansing component, which may or may not include added urea. In such an embodiment, the urea used to form the ionic liquid may not provide humectant properties, however, the added urea already contained in the cleansing component or the urea added to the cleansing component may provide humectant properties. In at least one embodiment, the urea in the solid cleansing composition is provided to form the ionic liquid with taurine, and a separate component/ingredient is provided to contribute humectant properties. For example, the solid cleansing composition may include urea and taurine for the ionic liquid, and glycerin for the humectant.

Free Fatty Acids

In at least one embodiment, the solid cleansing composition may include one or more free fatty acids configured to provide enhanced skin feel benefits. For example, the solid cleansing composition may include the fatty acids to provide softer or smoother feeling skin. Illustrative fatty acids may include, but are not limited to, vegetable oils, such as palm kernel oil, palm oil, coconut oil, olive oil, laurel oil, and the like, and combinations thereof. Illustrative fatty acids may also include animal fats, such as tallow. Illustrative fatty acids may also include, but are not limited to, fatty acid sources having fatty acid distributions similar or substantially similar to natural or synthetic fatty acid sources (e.g., natural animal fats or oils, natural vegetable fats or oils, individual fatty acids, etc.).

Optional Skin Care Agents

In some embodiment, the solid cleansing composition may include one or more skin care agents. Any suitable skin care agents that do not adversely affect the stability and/or efficacy of the solid cleansing composition may be used. In at least one embodiment, the skin care agent may include an emollient configured to maintain a soft, smooth, and pliable appearance to the skin. As is known by those skilled in the art, the emollients may function by remaining on the surface of the skin or in the stratum corneum to act as a lubricant, to reduce flaking, and/or to improve the appearance of the skin.

The skin care agents may generally include one or more polymers (e.g., polyvinylpyrrolidine), protein derivatives (e.g., derivatized hydrolyzed wheat protein), ethoxylated fatty ethers, cellulosics (e.g., hydroxyethylcellulose), and the like, and combinations thereof. Illustrative skin care agents may include, but are not limited to, esters comprising an aliphatic alcohol having about 2 to about 18 carbon atoms condensed with an aliphatic or aromatic carboxylic acid including about 8 to about 20 carbon atoms (e.g., isopropyl myristate, decyl oleate, cetearyl isononanate, etc.). The esters may be straight chained or branched. In a preferred embodiment, the ester has a molecular weight of less than about 500.

Other skin care agents may include, but are not limited to, polyvinyl-pyrrolidone, polyquaternium-4, polyquaternium-7, polyquaternium-10, guar gum derivatives, hydroxypropylmethylcellulose, hydroxyethylcellulose, a polyethylene glycol, a methyl ether of a polyethylene glycol, quaternium-79, wheat germamidopropyl hydroxypropyl dimonium hydrolyzed wheat protein, stearyl methicone, dimethicone copolyol, dimethicone propyl PG betaine, poly(sodium styrene sulfonate), sorbitan oleate, steareth-2, steareth-21, isoceteth-20, PEG-7 glyceryl cocoate, PEG-75 lanolin, glycereth-26, PPG-5-ceteth-20, a $C_{12}$-$C_{20}$ alcohol, canola oil, glyceryl laurate, triglyceryl monostearate, glyceryl monostearate, vitamin E acetate, sunflower seed amidopropylethyldimonium ethylsulfate, sodium PEG-7 olive oil carboxylate, PPG-1 hydroxyethyl caprylamide, PPG-2 hydroxyethyl cocamide, mineral oil, petrolatum, aloe barbadensis, isostearamidopropylmorpholine lactate, strontium acetate, palmitamidopropyltrimonium chloride, and the like, and combinations thereof. In a preferred embodiment, the skin care agent is or includes a conditioner, such as a cationic cellulose polymer (e.g., polyquaternium-7).

Salts

The solid cleansing composition may include one or more salts configured to modify the one or more surfactants of the solid cleansing composition. For example, the salts may be configured to at least partially modify a cloud point of the surfactants to thereby control the haze or transparency of the cleansing composition. The salts may be or include one or more inorganic salts including, but not limited to, sodium sulfate, magnesium sulfate, sodium chloride, sodium citrate, and the like, and combinations thereof. The amount of any one or more of the salts may be at least partially determined by the type and/or amount of the surfactants included in the solid cleansing composition. In at least one embodiment, the amount of any one or more of the salts may be about 0.1 wt %, 0.2 wt %, 0.3 wt %, 0.4 wt %, or 0.5 wt % to about 0.6 wt %, 0.7 wt %, 0.8 wt %, 0.9 wt %, or about 1.0 wt %.

Additional Optional Components/Ingredients

The solid cleansing composition may include one or more additional optional ingredients. Illustrative optional ingredients may include, but are not limited to, one or more dyes, fragrances, buffers and buffering agents (e.g., inorganic phosphates, sulfates, and carbonates), pH adjusters (e.g., acids and/or bases), preservatives (e.g., parabens, hydantoins, imidazolines, etc.), thickeners, viscosity modifiers, antioxidants, foam enhancers, chelating agents (e.g., EDTA, phosphates, pentasodium pentetate, etc.), skin conditioning agents, opacifiers, hydric solvents, hydrotropes, antimicrobials, sunscreen actives, anti-aging compounds, vitamins, essential oils and extracts (e.g., rosewood, jojoba, etc.), polyols, titanium dioxide, abrasives (e.g., particulate matter), and the like, and combinations thereof.

Illustrative antimicrobials may include, but are not limited to, triclocarban, triclosan, and the like, and combinations thereof. Illustrative anti-aging compounds may include, but are not limited to, alpha hydroxy acids, beta hydroxy acids, and the like, and combinations thereof. Illustrative sunscreen actives may include, but are not limited to, butyl methoxy benzoylmethane, and the like, and combinations thereof. Illustrative polyols may include, but are not limited to, glycerol, sorbitol, propylene glycol, polyethylene glycol, and the like, and combinations thereof. Illustrative abrasives or particulate matter may include, but are not limited to, silica, talc, calcium carbonate, polyethylene beads, jojoba beads, lufa, oat flour, and the like, and combinations thereof. Illustrative vitamins may include, but are not limited to, vitamins such as vitamin A, E, K, and C.

Illustrative basic pH adjusters may include ammonia; mono-, di-, and tri-alkyl amines; mono-, di-, and tri-alkanolamines; alkali metal and alkaline earth metal hydroxides; and the like, and combinations thereof. For example, the basic pH adjuster may be ammonia, sodium hydroxide, potassium hydroxide, lithium hydroxide, monoethanolamine, triethylamine, isopropanolamine, diethanolamine, triethanolamine, and the like, and combinations thereof.

Illustrative acidic pH adjusters may include mineral acids and polycarboxylic acids. The mineral acids may be or include hydrochloric acid, nitric acid, phosphoric acid, sulfuric acid, and the like, and combinations thereof. The polycarboxylic acids may be or include citric acid, glycolic acid, lactic acid, and the like, and combinations thereof.

The preservatives may be included in the liquid cleansing composition in an amount greater than 0.00 wt % and less than or equal to about 3.0 wt % or about 2.0 wt %. Illustrative preservatives may include, but are not limited to, benzalkonium chloride; benzethonium chloride, 5-bromo-5-nitro-1,3-dioxane; 2-bromo-2-nitropropane-1,3-diol; alkyl trimethyl ammonium bromide; N-(hydroxymethyl)-N-(1,3-dihydroxy methyl-2,5-dioxo-4-imidaxolidinyl-N-(hydroxy methyl)urea; 1-3-dimethyol-5,5-dimethyl hydantoin; formaldehyde; iodopropynl butyl carbamate, butyl paraben; ethyl paraben; methyl paraben; propyl paraben, mixture of methyl isothiazolinone/methyl-chloroisothiazoline in a 1:3 wt. ratio; mixture of phenoxythanol/butyl paraben/methyl paraben/propylparaben; 2-phenoxyethanol; tris-hydroxyethyl-hexahydrotriazine; methylisothiazolinone; 5-chloro-2-methyl-4-isothiazolin-3-one; 1,2-dibromo-2,4-dicyanobutane; 1-(3-chloroalkyl)-3,5,7-triaza-azoniaadamantane chloride; sodium benzoate; organic acids, sorbic acid, lactic acid, citric acid, and the like, and combinations thereof.

EXAMPLES

The following examples and other embodiments described herein are exemplary and not intended to be limiting in describing the full scope of compositions and methods of this disclosure. Equivalent changes, modifications and variations of specific embodiments, materials, compositions and methods may be made within the scope of the present disclosure, with substantially similar results.

Example 1

Various anhydrous ionic liquids (1)-(5) were prepared by combining the ingredients/components in the molar ratios and conditions according to Table 1. Urea and taurine were used to prepare each of the anhydrous ionic liquids (1)-(5). In each of the anhydrous 2:1 urea:taurine ionic liquids (1)-(4), a clear ionic liquid was observed. In the anhydrous 1:1 urea:taurine ionic liquid (5), small to minimal amounts of taurine crystals/precipitates were observed upon close inspection. The minimal amounts of taurine crystals/precipitates in the anhydrous 1:1 urea:taurine ionic liquid (5) demonstrates the ability to vary the molar ratios of this eutectic system over a broad range. For example, the ratio of urea to taurine may be from at least 1:1 to 2:1 or greater. It was further observed that heating under reflux reduced the preparation time dramatically. It was surprisingly and unexpectedly discovered that the melting of urea initiated the mixing with taurine.

TABLE 1

Anhydrous Urea-Taurine Ionic Liquids

| # | Urea:Taurine Ratio | Temperature (° C.) | Time Heated (hrs) | Heating Method |
|---|---|---|---|---|
| 1 | 2:1 | 120-130 | 96 | Oven |
| 2 | 2:1 | 120-130 | 24 | Hot Plate |
| 3 | 2:1 | 145-150 | 0.5 | Reflux |
| 4 | 2:1 | 120-130 | 2 | Reflux |
| 5 | 1:1 | 120-130 | 1 | Reflux |

Example 2

The anhydrous 2:1 urea to taurine ionic liquid (2) from Example 1 was studied in stability tests in comparison to a 5% taurine solution (6) and a 1:1 sulfuric acid to taurine mixture (7). The sulfuric acid in the 1:1 sulfuric acid to taurine mixture (7) protonates the taurine in a 1:1 ratio, and the 5% taurine solution was a 5% w/w aqueous taurine solution. As indicated in Table 2, each sample (2), (6), and (7) was tested in three different mediums and at two different taurine concentrations. The three different mediums tested included a blank medium containing only water, a 5% soap chip solution in water, and a 10% soap chip solution in water. The soap chips were prepared by combining the ingredients/components according to Table 3.

Each of the samples tested in Table 2 were prepared by adding the taurine solutions (2), (6), and (7) to the different mediums (water, 5% soap chip solution, and 10 % soap chip solution). Due to the relatively decreased solubility of the 5% Taurine solution (6) in comparison to the ionic liquid (2), all the taurine solutions (2), (6), and (7) were normalized via dilution of the ionic liquid (2). A drop of each of the samples (2), (6), and (7) was loaded onto a glass slide, and each of the glass slides was placed under a dust hood overnight. The results of the study are summarized below in Table 2.

TABLE 2

| # | No Soap | 5% Soap | 10% Soap |
|---|---|---|---|
| (2) Urea:Taurine (diluted) | No Precipitate | No Precipitate | No Precipitate |
| (6) 5% Taurine Soln (diluted) | Precipitate | Precipitate | Precipitate |
| (7) Sulfuric Acid Taurine (diluted) | Precipitate | Precipitate | Precipitate |
| (2) Urea:Taurine | No Precipitate | No Precipitate | No Precipitate |
| (6) 5% Taurine Soln. | Precipitate | No Precipitate | Precipitate |
| (7) Sulfuric Acid Taurine Complex | Precipitate | Precipitate | No Precipitate |

TABLE 3

| Ingredient/Component | Concentration (wt %) |
|---|---|
| Sodium Soap | 77.3 |
| Water | 15.0 |
| Glycerin | 4.5 |
| Free Fatty Acid | 1.5 |
| Sodium Chloride | 0.9 |
| Sodium Citrate | 0.6 |
| Balance | 0.13 |

TABLE 3-continued

| Ingredient/Component | Concentration (wt %) |
|---|---|
| Pentasodium Pentetate | 0.024 |
| Sodium Sulfate | 226.7 ppm |

As is evident from Table 2, the 5% taurine solution (6) and the sulfuric acid taurine complex (7) formed precipitate. As is further evident from Table 2, the anhydrous 2:1 urea:taurine ionic liquid (2) did not form precipitate.

Example 3

To mimic or emulate the accelerated crystallization of taurine in solid cleansing compositions (e.g., soap bars), soap noodle studies were performed on the anhydrous 2:1 urea to taurine ionic liquid (2) of Example 1, the 5% taurine solution (6) of Example 2, and the sulfuric acid-taurine complex (7) of Example 2. For the soap noodle studies, a soap slurry or soap chip solution was prepared by grinding up 45.0 g of the soap chips of Table 3 to a fine powder and mixing the soap chips with 15.0 g of water (about 1:0.3 weight ratio). Then, either 5.05 g of the anhydrous 2:1 urea to taurine ionic liquid (2), 5.00 g of the 5% taurine solution (6), or 5.07 g of the sulfuric acid-taurine complex (7) was added to separate soap chip solutions. A small portion (approx. less than 10 mL) of each of the soap chip solutions containing the anhydrous 2:1 urea to taurine ionic liquid (2), the 5% taurine solution (6), and the sulfuric acid-taurine complex (7) was transferred to respective syringes and squeezed out to form a "noodle" on respective glass slides in duplicates and allowed to age for three weeks. Each week, each of the noodles were viewed under a Stereo Microscope (Olympus SZX10) and photomicrographs of the noodles were analyzed. As the noodles age, water evaporates, resulting in noodles having a final composition of about 5 wt % taurine. The results of the soap noodle studies are summarized in Tables 4 and 5.

TABLE 4

| | Sulfuric Acid Taurine Solution (7) | | Urea Taurine Ionic Liquid (2) | |
|---|---|---|---|---|
| | 50° C. | RT | 50° C. | RT |
| Week 1 | Precipitate | Precipitate | No Precipitate | No Precipitate |
| Week 2 | Precipitate | Precipitate | No Precipitate | No Precipitate |
| Week 3 | Precipitate | Precipitate | No Precipitate | No Precipitate |

TABLE 5

| | 5% Taurine Solution (6) | | Urea Taurine Ionic Liquid (2) | |
|---|---|---|---|---|
| | 50° C. | RT | 50° C. | RT |
| Week 1 | Precipitate | Precipitate | No Precipitate | No Precipitate |
| Week 2 | Precipitate | Precipitate | No Precipitate | No Precipitate |

As is evident from Tables 4 and 5, crystals/precipitate formed in both the sulfuric acid taurine solution (7) and the 5% taurine solution (6) while no crystals formed in the anhydrous urea taurine ionic liquids (2). In addition to the foregoing, it was observed that the noodles containing the anhydrous urea-taurine ionic liquids (2) exhibited white liquid spots, which were indicative of the humectant properties of urea. The results indicated that the anhydrous urea-taurine ionic liquid (2) was capable of preventing crystallization of taurine in a simulated environment.

Example 4

An MTT colorimetric assay (HaCat Cells) dose response experiment was conducted to analyze cell viability, or the percentage of cells present after treatment. Particularly, the MTT colorimetric assay was conducted to determine cell viability of the anhydrous 2:1 urea to taurine ionic liquid (2) of Example 1 in comparison to taurine. The HaCat Cells were 60-70% confluent, and a PBS buffer was used for serial volumetric dilutions. The results of the MTT colorimetric assay are summarized in Table 6, and highlight the effectiveness of the ionic liquid form. Cell viability greater than 100% indicates cell growth or proliferation, and cell viability less than 100% indicates cell death.

TABLE 6

| Concentration of | Cell Viability (%) | |
|---|---|---|
| Taurine (w/w %) | (2) | Taurine |
| Untreated | 100 | 100 |
| 0.00001 | 137.7275 | 136.5776 |
| 0.00010 | 130.7046 | 119.6213 |
| 0.00100 | 133.9866 | 141.3371 |
| 0.01000 | 135.4332 | 146.5244 |
| 0.10000 | 70.43086 | 99.02736 |

As illustrated in Table 6, the anhydrous 2:1 urea to taurine ionic liquid (2) exhibited similar cell viability as taurine alone. This indicates that effectiveness of the anhydrous 2:1 urea to taurine ionic liquid (2) for skin cells growth is comparable to taurine alone.

Example 5

Various hydrated ionic liquids (8)-(13) were prepared by combining the ingredients/components in the molar ratios and conditions according to Table 7. Urea (commercially available from Avantor Performance Materials, Inc. of Center Valley, Pa.) and taurine (commercially available from Sigma Aldrich Corp. of St. Louis, Mo.) were used to prepare each of the hydrated ionic liquids (8)-(12). To prepare each of the hydrated ionic liquids (8)-(12), a water and urea slurry was first prepared by combining water and urea with one another, heating the water and urea slurry, and then combining the taurine with the heated water and urea slurry.

TABLE 7

| Hydrated Urea-Taurine Ionic Liquids | | | | | |
|---|---|---|---|---|---|
| # | Urea:Taurine Ratio | Water Concentration | Temperature (° C.) | Time (hrs) | Heating Method |
| 8, 9 | 2:1 | 0% (8) 4% (9) | 120 | 72 | Oven |
| 10, 11 | 2:1 | 20% (10) 25% (11) | 80 | 192 | Oven |
| 12 | 2:1 | 20% | 80 | 16 | Reflux |
| 13 | 2:1 | 1:1 H2O:IL | 65-75 | 0.9 | Reflux |

As is evident in Table 7, the overall reaction temperature and time required to prepare each of the hydrated ionic liquids (8)-(13) was surprisingly and unexpectedly reduced with the addition of water. Without being bound by theory, it is believed that the solubility of urea in the water facilitated the dissolution of the taurine.

Example 6

Soap noodle studies were performed on a control containing 5% taurine (15), an anhydrous 2:1 urea to taurine ionic liquid (14) (prepared similarly to (4), but heated for 30 hours), and a hydrated urea-taurine ionic liquid (12). The soap noodle studies, were performed similar to Example 3 above, and were performed to mimic or emulate the accelerated crystallization of taurine in solid cleansing compositions. The results of the soap noodle studies are summarized in Table 8.

TABLE 8

| | Control (15) | | Anhydrous 2:1 Urea Taurine Ionic Liquid (14) | | Hydrated Urea Taurine Ionic Liquid (12) | |
|---|---|---|---|---|---|---|
| | 50° C. | RT | 50° C. | RT | 50° C. | RT |
| Week 1 | Precipitate | Precipitate | No Precipitate | No Precipitate | No Precipitate | No Precipitate |
| Week 2 | Precipitate | Precipitate | No Precipitate | No Precipitate | No Precipitate | No Precipitate |

As is evident in Table 8, crystals/precipitate formed in the control (15), and no crystals formed in the anhydrous or hydrated urea taurine ionic liquids (14) and (12). In addition to the foregoing, it was surprisingly and unexpectedly discovered that the control (15) maintained at 50° C. had a brown color, while the ionic liquids (14) and (12) maintained their white color, which indicated that urea was able to stabilize the color of solid cleansing compositions as compared to taurine alone, as utilized in the control (15).

Accordingly, it has been surprisingly and unexpectedly discovered that taurine may be incorporated into solid cleansing compositions, such as bar soap compositions, via the eutectic system disclosed herein. Particularly, it has been discovered that both the anhydrous ionic liquids and the hydrated ionic liquids allow taurine to be incorporated into the solid cleansing compositions in appreciable and/or effective quantities. It has also been surprisingly and unexpectedly discovered that incorporating water in the eutectic system to form the hydrated ionic liquids significantly reduced the reaction temperatures and times for preparing the eutectic systems. Additionally, it was surprisingly and unexpectedly discovered that the ionic liquids and/or the base (e.g., urea) thereof maintains and/or preserves the color of the solid cleansing compositions, and further contributes to the overall moisture or humectant properties thereof.

The present disclosure has been described with reference to exemplary embodiments. Although a limited number of embodiments have been shown and described, it will be appreciated by those skilled in the art that changes may be made in these embodiments without departing from the principles and spirit of the preceding detailed description. It is intended that the present disclosure be construed as including all such modifications and alterations insofar as they come within the scope of the appended claims or the equivalents thereof.

What is claimed is:

1. A solid cleansing composition, comprising:
   a soap; and
   an ionic liquid comprising taurine and a Brønsted base selected from urea, arginine, lysine, acetamide, and guanidine.

2. The solid cleansing composition of claim 1, wherein the ionic liquid is an anhydrous ionic liquid having less than 0.5 wt % water based on a total weight of the ionic liquid.

3. The solid cleansing composition of claim 1, wherein the ionic liquid further comprises water.

4. The solid cleansing composition of claim 3, wherein the ionic liquid is a hydrated ionic liquid having greater than or equal to 0.5 wt % water based on a total weight of the ionic liquid.

5. The solid cleansing composition of claim 1, wherein a molar ratio of the Brønsted base to taurine is greater than or equal to 1:1.

6. The solid cleansing composition of claim 1, wherein a molar ratio of the Brønsted base to taurine is greater than 1:1 and less than or equal to 3:1.

7. The solid cleansing composition of claim 1, wherein a molar ratio of the Brønsted base to taurine is greater than 1:1 and less than or equal to 2.5:1.

8. The solid cleansing composition of claim 1, wherein a molar ratio of the Brønsted base to taurine is greater than 1:1 and less than or equal to 2:1.

9. The solid composition of claim 3, wherein a molar ratio of taurine to water is greater than or equal to 1:1.

10. The solid composition of claim 3, wherein a molar ratio of taurine to water is greater than 1:1 and less than or equal to 3:1.

11. The solid composition of claim 3, wherein a molar ratio of taurine to water is greater than 1:1 and less than or equal to 2:1.

12. The solid cleansing composition of claim 1, wherein the Brønsted base is urea.

13. The solid cleansing composition of claim 1, wherein the soap is a sodium soap, an ammonium soap, a potassium soap, a magnesium soap, a calcium soap, or a combination thereof.

14. The solid cleansing composition of claim 1, wherein the soap comprises alkali metal salts of aliphatic acids having 8 to 22 carbon atoms.

15. A method for preparing the solid cleansing composition of any one of the preceding claims, comprising:
    contacting the Brønsted base with taurine;
    heating the Brønsted base and taurine to form the ionic liquid; and
    contacting the ionic liquid with the soap.

16. The method of claim 15, further comprising contacting the Brønsted base with water to form a slurry before contacting the Brønsted base with taurine.

17. The method of claim 16, further comprising contacting the taurine with the slurry before heating the Brønsted base and taurine.

18. The method of claim 15, wherein heating the Brønsted base and taurine comprises heating the Brønsted base and taurine to a temperature greater than 80° C.

19. The method of claim 15, further comprising melting the Brønsted base before solubilizing taurine.

20. A solid cleansing composition, comprising:
    a soap selected from the group consisting of a sodium soap, an ammonium soap, a potassium soap, a magnesium soap, a calcium soap, or a combination thereof; and
    an ionic liquid comprising urea and taurine, wherein the ionic liquid is an anhydrous ionic liquid having less than 0.05 wt % water based on a total weight of the ionic liquid, and wherein a molar ratio of the urea to taurine is greater than 1:1 and less than or equal to 3:1.

* * * * *